United States Patent [19]

Shah et al.

[11] Patent Number: 5,482,718
[45] Date of Patent: Jan. 9, 1996

[54] COLON-TARGETED DELIVERY SYSTEM

[75] Inventors: Navnit H. Shah, Clifton; Wantanee Phuapradit, Kearny; Aruna Railkar, Clifton, all of N.J.

[73] Assignee: Hoffmann-La Roche Inc., Nutley, N.J.

[21] Appl. No.: 217,344

[22] Filed: Mar. 23, 1994

[51] Int. Cl.$^6$ .............................. A61K 9/30; A61K 9/32; A61K 9/36
[52] U.S. Cl. .......................... 424/480; 424/474; 424/475; 424/482; 424/468
[58] Field of Search .................. 424/474, 475, 424/480, 482

[56] References Cited

U.S. PATENT DOCUMENTS

| | | | |
|---|---|---|---|
| 4,432,966 | 2/1984 | Zeitoun et al. | 424/21 |
| 4,525,339 | 6/1985 | Behl et al. | 424/16 |
| 4,668,517 | 5/1987 | Weber et al. | 424/469 |
| 4,871,549 | 10/1989 | Ueda et al. | 424/494 |
| 4,892,742 | 1/1990 | Shah | 424/480 |
| 5,171,580 | 12/1992 | Iamartino et al. | 424/490 |
| 5,225,202 | 7/1993 | Hodges et al. | 424/480 |

OTHER PUBLICATIONS

Saffran, et al., Science, 233: pp. 1081–1084, (Sep. 5, 1986).
Hardy, et al., J. Pharm. Pharmacol., 37: pp. 874–877 (Apr. 4, 1985).
Dew, et al., British J. of Clini. Pharm., 14: pp. 405–408, (1982).

*Primary Examiner*—Thurman K. Page
*Assistant Examiner*—James M. Spear
*Attorney, Agent, or Firm*—George M. Gould; William H. Epstein; Bruce A. Pokras

[57] ABSTRACT

A novel delivery system for targeting drugs to the colon is disclosed. The delivery system is a tablet comprised of three parts: (1) an enteric coating to prevent penetration of gastric fluid into the delivery system, thereby preventing any drug release in the stomach; (2) an erodible polymer layer which is exposed and gradually erodes during transit through the upper intestinal tract, and (3) a core, which is a conventional tablet or beadlet containing an active ingredient(s), which readily disintegrates and subsequently releases the drug to the target site, the colon, after erosion of the erodible polymer layer. The erodible polymer layer prevents drug release in the upper portion of the intestinal tract for 4–6 hours after gastric emptying, representing the amount of time needed for the delivery system to reach the colon.

5 Claims, 3 Drawing Sheets

COLON-TARGETED DELIVERY SYSTEM

BACKGROUND OF THE INVENTION

Targeting of drugs to the colon through oral administration of drugs is attractive and important for two reasons: 1) large bowel diseases, such as ulcerative colitis or Crohn's Disease, can be treated locally, thus avoiding enema dosage forms and minimizing systemic absorption; and 2) drugs that may be absorbed in the colon but which are degraded in the upper digestive tract (e.g., protein and peptide drugs), can be made available orally, since the colonic site minimizes the exposure of these compounds to the multitude of degradative digestive and proteolytic enzymes present in the upper digestive tract. Even though it would be expected that the absorption of most drugs from the colon is slower than from the small intestine, this is balanced by the longer residence time (17–72 hours) in the colon (1).

Dew et al. (2) reported that the application of a Eudragit S based coating (which is widely used to produce acid resistant formulations) is reasonably effective in the release of drug in the ascending colon. The concept of enteric coating to deliver drugs to the colon is thus proposed. However, Eudragit S dissolves above pH 7. If the pH of the upper intestinal tract reaches 7, then this Eudragit S coating will dissolve and the dosage form will release drug prior to reaching the colon. Saffran et al. (3) reported the use of azo polymers for colonic delivery. These polymers are degraded by colonic bacterial azo-reductase activity, but are unaffected by acid conditions or action of gastrointestinal enzymes, and therefore could be used as potential coatings for colonic delivery. However, these coatings depend on the presence of colonic anaerobic bacteria for their optimum performance. Also, the safety of these polymers is not well established.

A system based on a time-controlled explosion mechanism is described in U.S. Pat. No. 4,871,549 in which drug release is caused by explosion of a membrane after a definite time period (4). The system was described for various types of controlled release applications. The formulations only had a semipermeable membrane coating, thus the system would start operating once the dosage form was in contact with gastrointestinal fluid, irrespective of whether the fluid was gastric or intestinal.

A delivery system for targeting the colon is described in U.S. Pat. No. 5,171,580. This delivery system consists of an enteric outer coating, a high viscosity grade of hydrophilic polymer layer which can swell when exposed to the intestinal fluid, and an anionic copolymer inner layer, EUDRAGIT S, which is soluble at a pH above 7.0, surrounding a core containing the active ingredient. Due to a small quantity of liquid in the colon, therefore, the use of high viscosity grade of polymer could diminish the drug availability to be absorbed if the dosage form reached to the colon prior to complete dissolution of the polymer. Moreover, the swelling nature of the high viscosity grade of polymer could cause cracking of the enteric coating, resulting in failure of the delivery system, if even a small amount of gastric fluid penetrated the enteric coating during the time that the delivery system stays in the stomach.

SUMMARY OF THE INVENTION

A novel delivery system for targeting drugs to the colon is herein described. The delivery system is a tablet comprised of three parts:

(1) enteric coating: The outer enteric coating prevents penetration of gastric fluid into the delivery system, thereby preventing any drug release in the stomach;

(2) erodible polymer layer: Once the dosage form is emptied into the intestine, the enteric coat dissolves and then a pH-independent, non-swelling, erodible polymer, such as a low viscosity (3–100 cps @ 2% w/w in water) grade of a cellulose ether derivative, is exposed and gradually erodes during transit through the upper intestinal tract. The erodible polymer layer prevents drug release in the upper portion of the intestinal tract for 4–6 hours after gastric emptying, representing the amount of time needed to reach the colon; and (3) core: The core is a conventional tablet or beadlet containing an active ingredient(s) which readily disintegrates, and subsequently releases the drug to the colon after erosion of the erodible polymer layer.

DETAILED DESCRIPTION OF THE INVENTION

A novel delivery system for administering drugs to the colon is herein described. The delivery system is a tablet comprised of three layers: 1) a core containing the drug; 2) a non-swelling, erodible polymer layer surrounding the core (with the combination of core and erodible polymer layer being referred to as the "dual matrix tablet"); and 3) an enteric coating applied to the dual matrix tablet. The composition and function of the components of the delivery system of the invention are further described as follows:

(1) Enteric coating: The outer enteric coating prevents penetration of gastric fluid into the delivery system, thereby preventing any drug release in the stomach. Any conventional enteric coating materials may be used in the delivery system of the invention. Examples of enteric coating materials are hydroxypropyl methylcellulose phthalate, polyvinyl acetate phthalate or methacrylic acid copolymers. Preferred is a methacrylic acid/methyl methacrylate copolymer having a ratio of free carboxyl groups to the ester groups of about 1:1, and which dissolves in media at and above pH 6 (e.g., EUDRAGIT L100 (Rohm Pharma Co.)). Especially preferred are hydroxypropyl methylcellulose phthalates ("HPMCP") which dissolve in media at and above pH 5.5 (e.g., HPMCP-55, Eastman Chemical Co.; HP-55, Shin-Etsu Chemicals Co.). The percent content range (by weight) of methoxy groups, hydroxypropoxy groups and carboxybenzoyl groups in the preferred HPMCP for use in the invention is 18–22%, 4–9%, and 27–35%, respectively.

The enteric coating materials are preferably formulated with appropriate plasticizers, such as distilled acetylated monoglycerides or triethyl citrate. The preferred plasticizer is a distilled acetylated monoglyceride derived from partially hydrogenated soybean oil which has been fully ($\geq$96%)acetylated (e.g., MYVACET 9-45 (Eastman Chemical Co.)). The enteric coatings may be applied to the dual matrix tablet by any conventional means. For example, the dual matrix tablet may be coated using a suitable air spray system. A coating weight of approximately 5–25% (most preferred is 15%) by weight of the final tablet is recommended depending on the degree of acid resistance of the enteric coating material. A coating thickness of from about 50 µm to about 300 µm, preferably 100 µm, should be used, depending upon the type of polymer and plasticizer used.

(2) Erodible polymer layer: Once the tablet is emptied into the intestine, the enteric coating dissolves and then a layer of a pH-independent erodible polymer, such as a low viscosity grade of a cellulose ether derivative, is exposed and gradually erodes during transit through the upper intestinal tract. The erodible polymer layer preferably comprises 30–85% of the weight of the final tablet. The thickness of the erodible polymer layer is from about 2.0 mm to about 3.5 mm, preferably about 3.0 mm. By "low viscosity" is meant a cellulose ether derivative having a viscosity of 3–100 cps at a concentration of 2% w/w in water. Such low viscosity cellulose ether derivatives produce negligible swelling upon exposure to the intestinal juice. The lack of swelling of the polymer will prevent cracking of the enteric coating if any minimal permeation of gastric fluid through the enteric coating occurs during the period the delivery system stays in the stomach. The erodible polymer layer prevents drug release in the upper portion of the intestinal tract for 4–6 hours after gastric emptying, representing the amount of time needed for the delivery system to reach the colon.

Examples of cellulose ether derivatives that can be suitably employed for the erodible polymer layer in accordance with this invention include low viscosity hydroxypropyl methylcellulose, low viscosity hydroxypropyl cellulose or their mixtures. The preferred polymer is low viscosity hydroxypropyl methylcellulose. One example is a hydroxypropyl methylcellulose having a methoxy percent of 19–24% with a methoxy degree of substitution range from 1.1 to 1.6 and hydroxypropyl percent of 7–12% with a hydroxypropyl molar substitution range from 0.1–0.3 (e.g., METHOCEL K (Dow Chemical Corp.). Preferred is a hydroxypropyl methylcellulose having a methoxy percent of 28–30% with a methoxy degree of substitution range from 1.8 to 2.0 and hydroxypropyl percent of 7–12% with a hydroxypropyl molar substitution range from 0.2–0.3 having a viscosity (2% w/w in water) of 5–7 cps (e.g., METHOCEL E6 (Dow Chemical Corp.)) or 13–18 cps (e.g., METHOCEL E15LV (Dow Chemical Corp.)). The preferred molecular weight of any of the hydroxypropyl methylcelluloses is from 10,000 to 26,000 Da.

The erodible polymer layer is preferably formulated as a mixture of the cellulose ether derivative with a microcrystalline cellulose. The preferred microcrystalline cellulose has a moisture content of about 5% and an average particle size of about 100 microns (e.g., AVICEL PH 102 (FMC Corp.)). The weight ratio of cellulose ether derivative to microcrystalline cellulose is preferably from about 6:1 to about 0.5:1. The erodible polymer layer ingredients may be granulated with a binding agent such as a polyvinyl pyrrolidone. Preferred polyvinyl pyrrolidones have average molecular weights from about 40,000 Da (e.g., POVIDONE K30 (BASF, Midland, Mich.)) to about 360,000 Da (e.g., POVIDONE K90) (BASF, Midland, Mich.)). The granulation is preferably screened to a fine powder through a #40–#60 mesh screen and then lubricated with a conventional lubricant, e.g., magnesium stearate. Excipients, such as lactose, may also be incorporated into the erodible polymer layer for modifying the erosion profile.

(3) Core: The core is a conventional tablet or beadlet containing an active ingredient(s) in a pharmaceutically acceptable carrier which readily disintegrates and subsequently releases the drug to the colon after erosion of the erodible polymer layer. The core is preferably comprised of drug, diluent, disintegrant, binder and lubricant. Any conventional tablet formulating materials may be used to produce the core. The preferred disintegrant is croscarmellose sodium (e.g., AC-DI-SOL, FMC Corp., Philadelphia, Pa.). The cores may be prepared by any conventional means known in the tablet-forming art. For example, the cores may be prepared either by a direct compression method or by a wet granulation method using a suitable .tablet compaction press. Preferably, the granulation is compressed into a tablet having a weight of approximately 100 mg and a hardness of about 4–5 scu. The core comprises 10–45% of the weight of the final tablet.

The enteric coating of the drug delivery system of the present invention prevents the system from operating until the system leaves the stomach. Therefore, variations in gastric residence time do not influence the performance of the invention. Due to the pH-independent properties of the erodible polymer, variations in intestinal pH do not affect the onset of drug release. Once the erodible polymer layer completely erodes, drug release from the core will occur within a relatively short time period and be available for absorption at the target site, the colon.

BRIEF DESCRIPTION OF THE DRAWINGS

A schematic presentation illustrating the release mechanism of the delivery system of the invention is depicted in FIG. 1.

Figure 1:
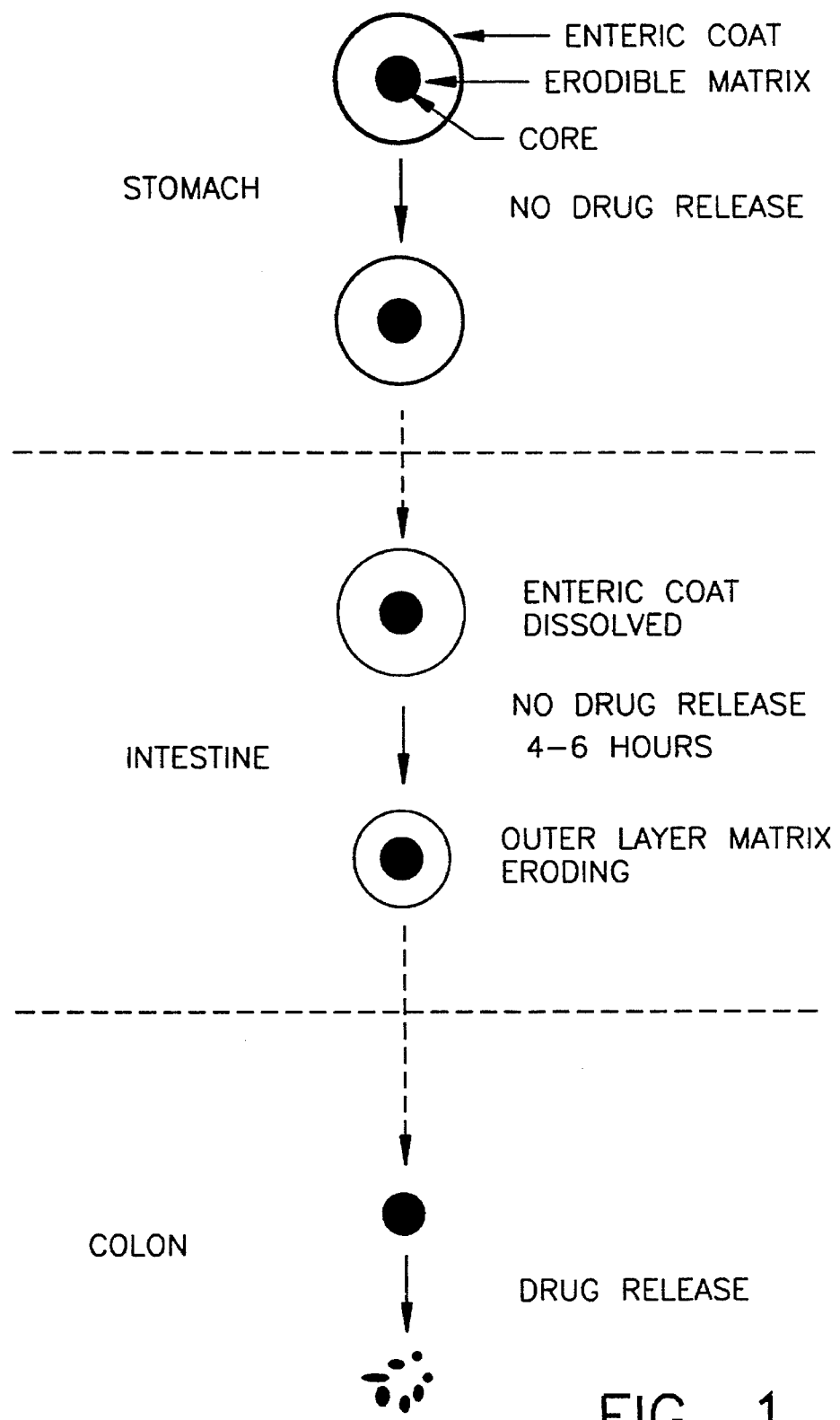

The dual matrix tablet containing the core and the erodible polymer layer may be prepared by any conventional means. For example, using a suitable tablet compaction press, half of the erodible polymer layer matrix granulation may be placed in the die cavity, and the core, previously prepared, is centered in the die cavity. The other half of the erodible polymer layer matrix granulation is placed in the die cavity and the mass may then be compressed at a suitable pressure, e.g., 5,000 lbs. Alternatively dual matrix tablets could be prepared using compression coating technique with a Dri-Coata Tablet Press.

The viscosity of a cellulose ether derivative for use in practicing the present invention is determined by a suitable viscometer of the Ubbelohde type as directed under "Viscosity" on page 1619 of U.S. Pharmacopeia (USP) XXII & National Formulary (NF) XVII (The United States Pharmacopeial Convention, Inc., Rockville, Md. 1990)

The determination of the ability of a delivery system of the invention to deliver an active ingredient to the colon may be performed using the USP dissolution test procedure with Basket Method at the speed as specified. The Basket Method is described on page 1578 of U.S. Pharmacopeia-(USP) XXII & National Formulary (NF) XVII (The United States Pharmacopeial Convention, Inc., Rockville, Md. 1990).

The delivery system is placed in the basket and the basket is immersed in 900 mL of simulated gastric fluid without enzyme controlled at 37° C. The basket is rotated at a speed of 100 rpm for 4 hours to determine if the integrity of the enteric coating will be maintained during gastric residence. The basket containing the delivery system is removed from the simulated gastric fluid and then immersed and rotated at 100 rpm at 37° C. in simulated intestinal fluid without enzyme to determine the amount of time needed for the erodible polymer layer to completely erode and release the active ingredient. This amount of time is preferably 4–6 hours. The amount of drug released from the delivery system into the simulated intestinal fluid is quantitatively determined using UV spectrophotometry. In this manner, the suitability and the quantitative compositions of materials for use in the enteric coating, erodible polymer layer and core, may be routinely determined.

The following examples illustrate means and methods of carrying out the present invention. The examples are only illustrative and should not be considered as limiting the scope of the invention. 2-Hydroxy-4-[5-(2,3-dihydroxyphenyl) pentyloxyl]-3-propyl-benzoic acid and 5-aminosalicylic acid, which are drugs being investigated for the treatment of inflammatory bowel diseases, were selected as model drugs in this study.

EXAMPLE I

| 2-Hydroxy-4-[5-(2,3-dihydroxyphenyl) pentyloxyl]-3-propyl-benzoic acid: 40 mg Tablets | |
|---|---|
| | mg/tablet |
| Core | |
| 2-hydroxy-4-[5-(2,3-dihydroxyphenyl)-pentyloxyl]-3-propyl-benzoic acid | 40.00 |
| microcrystalline cellulose | 25.00 |
| croscarmellose sodium | 10.00 |
| mannitol | 20.00 |
| polyvinyl pyrrolidone | 4.00 |
| magnesium stearate | 1.00 |
| Erodible polymer layer | |
| hydroxypropyl methylcellulose | 416.25 |
| microcrystalline cellulose | 75.00 |
| polyvinyl pyrrolidone | 6.25 |
| magnesium stearate | 2.50 |
| Enteric Coating | |
| hydroxypropyl methylcellulose phthalate | 54.55 |
| distilled acetylated monoglycerides | 5.45 |
| Total Tablet Weight | 660.00 |

Preparation:

A. Preparation of Core 1. 2-Hydroxy-4-[5-(2,3-dihydroxyphenyl) pentyloxyl]-3-propyl-benzoic acid, microcrystalline cellulose (AVICEL PH102), croscarmellose sodium (ACDISOL) and mannitol were mixed in a Hobart Mixer for 15 minutes.
2. The powder mix from Step 1 was granulated with 20% polyvinyl pyrrolidone (POVIDONE K30) solution until the optimum granulation was obtained.
3. The granulation from Step 2 was dried overnight at 50° C.
4. The granulation from Step 3 was passed through a #30 mesh screen.
5. The granulation from Step 4 was blended with magnesium stearate.
6. Using an F-Press and a ¼" standard concave round punch, the granulation was compressed into a tablet having a weight of 100 mg and a hardness of 4–5 scu.

B. Preparation of erodible polymer layer and dual matrix tablets

1. Hydroxypropyl methylcellulose (METHOCEL E6), microcrystalline cellulose (AVICEL PH 102) and polyvinyl pyrrolidone (POVIDONE K90) were uniformly mixed in a mortar.
2. The powder mix was granulated with 50% v/v alcohol solution until the optimum granulation was obtained.
3. The granulation from Step 2 was dried overnight at 50° C.
4. The granulation from Step 3 was passed through a #40 mesh screen.
5. The granulation from Step 4 was blended with magnesium stearate.
6. Using a Carver Press and a 7/16" standard concave round punch, half of the granulation from Step 5 (based on tablet weight) was placed in the die cavity, and the inner matrix core) from Step A.6 was centered in the die cavity. The other half of the granulation from Step 5 was placed in the die cavity and the mass was then compressed at 5000 lbs.

C. Enteric Coating

1. Using a propeller mixer, 42 g of hydroxypropyl methylcellulose phthalate (HPMCP-55) and 4.2 g of distilled acetylated monoglycerides (MYVACET 9-45) were dissolved in a 514 mL of a mixture of acetone and absolute alcohol (1:1).
2. Using a spraying system, the dual matrix tablets from Step B.6 were coated with the solution from Step 1 until the tablets were properly coated. Approximately 60 mg of the coating material (dry basis) was applied per tablet.

Testing:

The determination of the ability of a delivery system of the invention to deliver an active ingredient to the colon was performed using the USP dissolution test procedure Basket Method at the speed as specified. The Basket Method is described on page 1578 of U.S. Pharmacopeia (USP) XXII & National Formulary (NF) XVII (The United States Pharmacopeial Convention, Inc., Rockville, Md. 1990).

The assembly used in the Basket Method consists of the following: a covered vessel made of glass with nominal capacity 1000 mL; a motor; a cylindrical basket; and a metallic drive shaft for rotating the cylindrical basket. The vessel containing 900 mL of the specified dissolution medium is partially immersed in a suitable thermostatically-controlled, heated water bath and equilibrated at 37°±0.5° C. A fitted cover may be used to retard evaporation. The shaft is positioned so that its axis is not more than 2 mm at any point from the vertical axis of the vessel and rotates smoothly and without significant wobble. The distance between the inside bottom of the vessel and the cylindrical basket is maintained at 25±2 mm during the test.

The vessel was filled with 900 mL of simulated gastric fluid (0.1N hydrochloric solution), and the temperature was equilibrated at 37° C. The delivery system was placed in the basket, and the basket containing the delivery system was immersed in the simulated gastric fluid and attached to the shaft. The basket was then rotated at a speed of 100 rpm for 4 hours to mimic the gastric residence time.

The basket with the delivery system was then removed from the simulated gastric fluid and immersed in simulated intestinal fluid (0.05M phosphate buffer, pH 7.5) and rotated at 100 rpm for at least 10 hours.

Figure 2:
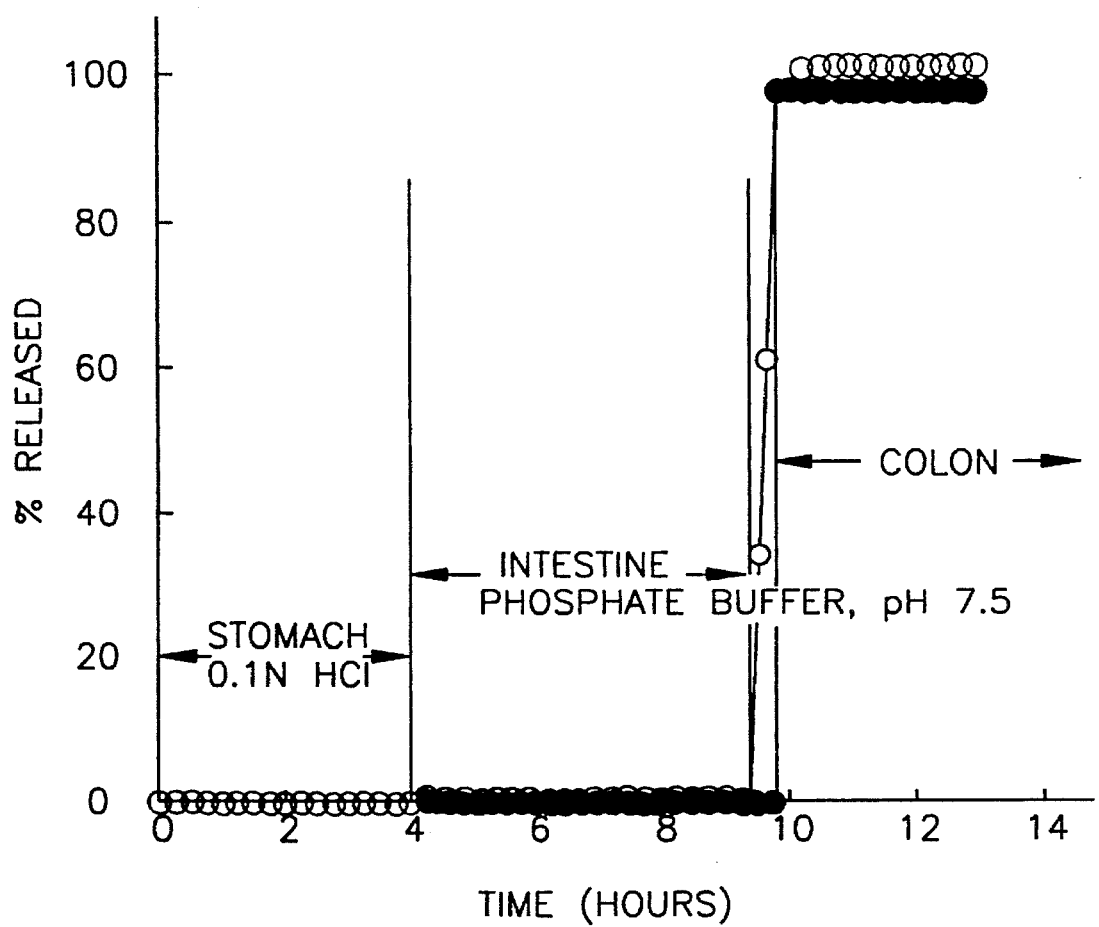
FIGS. 2 and 3 show release profiles of delivery systems.

The amount of drug release from the delivery system was quantitatively determined at regular intervals over at least 10 hours using UV spectrophotometry. The release profiles for two experiments are shown in FIG. 2. In the experiment represented by the open circle, the delivery system was exposed to both simulated gastric fluid and simulated intestinal fluid, as described above. In the control experiment represented by the solid circle, the delivery system was exposed only to the simulated intestinal fluid. FIG. 2 shows that the release profiles of both delivery systems are essentially identical. These results demonstrate that drug release will occur in a consistent manner regardless of differences in gastric emptying time.

Example II

5-Aminosalicylic Acid 40 mg Tablets

| | mg/tablet |
|---|---|
| Core | |
| 5-aminosalicylic acid | 40.00 |
| microcrystalline cellulose | 25.00 |
| croscarmellose sodium | 10.00 |
| mannitol | 20.00 |
| polyvinyl pyrrolidone | 4.00 |
| magnesium stearate | 1.00 |
| Erodible Polymer Layer | |
| hydroxypropyl methylcellulose | 166.70 |
| microcrystalline cellulose | 280.80 |
| polyvinyl pyrrolidone | 50.00 |
| magnesium stearate | 2.50 |
| Enteric Coating | |
| hydroxypropyl methylcellulose phthalate | 81.82 |
| distilled acetylated monoglycerides | 8.18 |
| Total Tablet Weight | 690.00 |

Preparation:
A. Preparation of Core
 1. 5-Aminosalicylic acid, microcrystalline cellulose (AVICEL PH 102), croscarmellose sodium (AC-DI-SOL) and mannitol were mixed in a Hobart Mixer for 15 minutes.
 2. The powder mix from Step 1 was granulated with 20% polyvinyl pyrrolidone (POVIDONE K30) solution until the optimum granulation was obtained.
 3. The granulation from Step 2 was dried overnight at 50° C.
 4. The granulation from Step 3 was passed through a #30 mesh screen.
 5. The granulation from Step 4 was blended with magnesium stearate.
 6. Using an F-Press and a ¼" standard concave round punch, the granulation was compressed into a tablet having a weight of 100 mg and a hardness of 4–5 scu.

B. Preparation of erodible polymer layer and dual matrix tablets
 1. Hydroxymethyl propylcellulose (METHOCEL E15LV), microcrystalline cellulose (AVICEL PH 102) and polyvinyl pyrrolidone (POVIDONE K30) were uniformly mixed in a mortar.
 2. The powder mix was granulated with 50% v/v alcohol solution until the optimum granulation was obtained.
 3. The granulation from Step 2 was dried overnight at 50° C.
 4. The granulation from Step 3 was passed through a #40 mesh screen.
 5. The granulation from Step 4 was blended with magnesium stearate.
 6. Using a Carver Press and a ¼" standard concave round punch, half of the granulation from Step 5 (based on tablet weight) was placed in the die cavity, and the inner matrix (core) from Step A.6 was centered in the die cavity. The other half of the granulation from Step 5 was placed in the die cavity and the mass were then be compressed at 5000 lbs.

C. Enteric Coating
 1. Using a Propeller Mixer, 42 g of hydroxypropyl methylcellulose phthalate (HPMCP-55) and 4.2 g of distilled acetylated monoglycerides (MYVACET 9-45) were dissolved in 514 mL of a solvent mixture of acetone and absolute alcohol (1:1).
 2. Using a spraying system, the dual matrix tablets from Step B.6 were coated with the solution from Step 1 until the tablets were properly coated. Approximately 90 mg of the coating material (dry basis) was applied per tablet.

Figure 3:
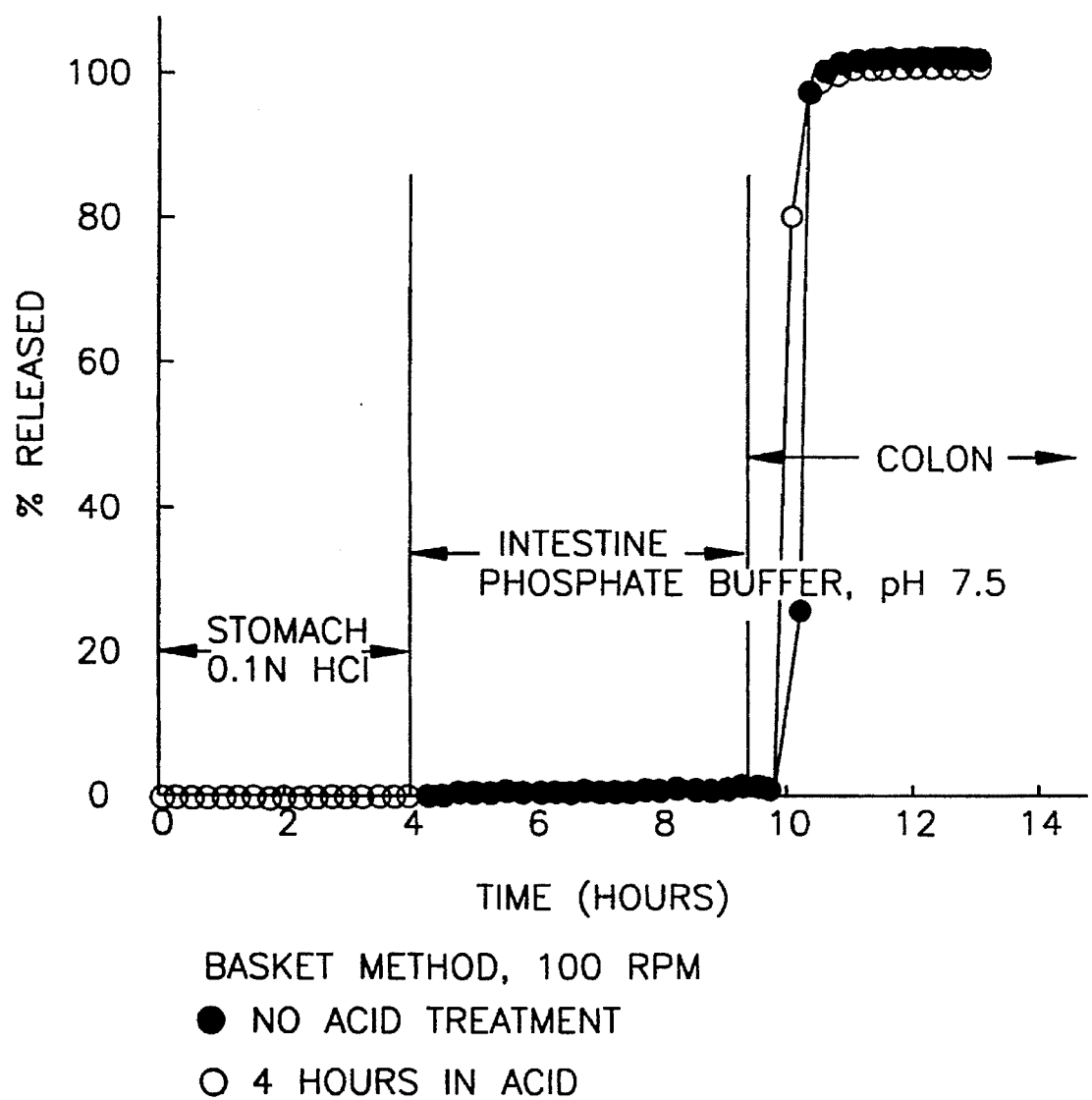

Testing:
 The procedure of Example I was followed.
 The amount of drug release from the delivery system was quantitatively determined using UV spectrophotometry. The release profiles for two experiments are shown in FIG. 3. In the experiment represented by the open circle, the delivery system was exposed to both simulated gastric fluid and simulated intestinal fluid, as described above. In the control experiment represented by the solid circle, the delivery system was exposed only to the simulated intestinal fluid. The release profiles of both delivery systems were found to be essentially identical. These results demonstrate that drug release will occur in a consistent manner regardless of differences in gastric emptying time.

REFERENCES

1. J. G. Hardy, C. G. Wilson and E. Wood, "Drug delivery to the proximal colon", J. Pharm. Pharmacol., 37: 874–877 (1985).
2. M. J. Dew, P. J. Hughes, M. G. Lee, B. K. Evans and J. Rhodes, Br. J. Clin.Pharmacol., 14: 405–408 (1982).
3. M. Saffran, G. S. Kumar, C. Savariar, J. C. Burnham, F. Williams and D. C. Neckers, "A new approach to the oral administration of insulin and other peptide drugs", Science, 233: 1081–1084 (1986).
4. Y. Ueda; T. Hata, H. Yamaguchi, S. Ueda and M. Kodami, U.S. Pat. No.4,871,549 (1989).

We claim:
1. A tablet suitable for a single oral administration being formed from the following:
 1) an inner core comprising 10–45% by weight of the tablet which comprises a biologically active compound and a pharmaceutically acceptable carrier;
 2) an erodible polymer layer which encases said inner core wherein said erodible polymer layer is 30–85% by weight of the tablet and has a thickness from about 2.0 mm to about 3.5 mm and comprises a pharmaceutically acceptable cellulose ether having a viscosity of 3–100 cps at a concentration of 2% w/w in water; and
 3) an enteric layer which encases said erodible polymer layer and core wherein said enteric layer is 5–25% by weight of the tablet and has a thickness from about 50 μm to about 300 μm.

2. The unit dosage form of claim 1 wherein said erodible polymer layer further comprises microcrystalline cellulose wherein the weight ratio of cellulose ether to microcrystalline cellulose is from about 6:1 to about 0.5:1.

3. The unit dosage form of claim 2 wherein the cellulose ether is selected from the group consisting of hydroxypropyl cellulose and hydroxypropyl methylcellulose, or mixtures thereof.

4. The unit dosage form of claim 3 wherein the cellulose ether is hydroxypropyl methylcellulose.

5. The unit dosage form of claim 4 wherein the hydroxypropyl methylcellulose has a methoxy percent of 19–30 with a methoxy degree of substitution of 1.1–2, a hydroxypropyl percent of 7–12 with molar substitution of 0.1–0.3 and a molecular weight of about 10,000–26,000 daltons.

* * * * *